US009474746B2

(12) United States Patent
Mahadevan et al.

(10) Patent No.: US 9,474,746 B2
(45) Date of Patent: Oct. 25, 2016

(54) METHODS FOR STABILIZING OXIDATIVELY UNSTABLE COMPOSITIONS

(71) Applicant: Johnson & Johnson Vision Care, Inc., Jacksonville, FL (US)

(72) Inventors: Shivkumar Mahadevan, Orange Park, FL (US); Frank Molock, Orange Park, FL (US); Vandeeta Khanolkar, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 377 days.

(21) Appl. No.: 13/894,482

(22) Filed: May 15, 2013

(65) Prior Publication Data

US 2014/0011843 A1    Jan. 9, 2014

Related U.S. Application Data

(62) Division of application No. 11/686,988, filed on Mar. 16, 2007, now Pat. No. 8,466,174.

(60) Provisional application No. 60/783,557, filed on Mar. 17, 2006.

(51) Int. Cl.
*A61K 31/4535* (2006.01)
*A61K 47/18* (2006.01)
*A61K 9/00* (2006.01)

(52) U.S. Cl.
CPC ......... *A61K 31/4535* (2013.01); *A61K 9/0048* (2013.01); *A61K 47/18* (2013.01); *A61K 47/183* (2013.01)

(58) Field of Classification Search
None
See application file for complete search history.

(56) References Cited

U.S. PATENT DOCUMENTS

| | | | |
|---|---|---|---|
| 4,304,762 | A | 12/1981 | Leigh |
| 5,876,695 | A | 3/1999 | Gries |
| 5,980,882 | A | 11/1999 | Eichman |
| 6,020,373 | A | 2/2000 | Schellenberg |
| 6,395,756 | B2 | 5/2002 | Trimming |
| 6,468,548 | B1 | 10/2002 | Kis |
| 6,576,649 | B1 | 6/2003 | Kis |
| 2002/0165254 | A1 | 11/2002 | Kis |
| 2004/0137068 | A1 | 7/2004 | Bhushan |

FOREIGN PATENT DOCUMENTS

| | | |
|---|---|---|
| DE | 150694 | 9/1981 |
| EP | 1172098 A1 | 1/2002 |
| EP | 1769834 A2 | 4/2007 |
| EP | 1172098 B1 | 12/2010 |
| JP | 02096531 A | 4/1990 |
| JP | 07324034 A | 12/1995 |
| JP | 11189528 A | 7/1999 |
| JP | 11510480 | 9/1999 |
| JP | 11279205 A | 10/1999 |
| JP | 2004509925 A | 4/2004 |
| JP | 2004516099 A | 6/2004 |
| JP | 2005509665 A | 4/2005 |
| JP | 2005514428 A | 5/2005 |
| KR | 20010024508 A | 3/2001 |
| RU | 2191012 C1 | 10/2002 |
| RU | 2201213 C1 | 3/2003 |
| WO | 9525518 A1 | 9/1995 |
| WO | WO 9700669 A1 | 1/1997 |
| WO | WO 9936055 A1 | 7/1999 |
| WO | WO 9951230 A1 | 10/1999 |
| WO | WO 0226277 A2 | 4/2002 |
| WO | WO 02051452 A1 | 7/2002 |
| WO | WO 03043660 A2 | 5/2003 |
| WO | WO 03059069 A1 | 7/2003 |
| WO | WO 2004058289 A1 | 7/2004 |
| WO | WO 2005089715 A1 | 9/2005 |

OTHER PUBLICATIONS

Norvell (Soil Science of America Journal, 48(6): 1285-1292, 1984).*
Adler, F.H. 1959 Physiology of the Eye. Third edition. p. 40.
Brawner, L.W. and Jessop, D.G. 1962 A review of contact lens solutions. Contacto 6:49-51.
Al-Subu, M.M. et al. "Osmium (VIII)-Catalyzed Oxidation of some Cyclic Amines by Potassium Hexacyanofernate(III) in Alkaline Media: A Kinetics and Mechanistic Study" Chemistry of Heterocyclic Compounds vol. 39, No. 4, 2003, pp. 478-484.
Chambron et al., "Interlacing Molecular Threads on Transition Metals" Pure & Appl. Chem., 1990, vol. 62, No. 6, pp. 1027-1034.
Larsen, Jan, et al., Journal of the Chemical Society, Perkin Transactions 2, A Facile Oxidation of Secondary Amines to Imines by Iodosobenzene or by a Terminal Oxidant and Manganese or Iron Porphyrins and Manganese Salen as the Catalysts, 1992, pp. 1213-1217.
Leigh et al., "Benzylic Imine Catenates: Readily Accessible Octahedral Analogues of the Sauvage Catenates", Angew. Chen Int. Ed., 2001, 40, No. 8, pp. 1538-1542.
Perrigin et al., Investigative Ophthalmology & Visual Science, 2004; 45: E-Abstract, 2004.
Prince, A.K., Ann. N.Y. Acad. Sci., 1960, 88, 512-518, Chelation and Catalysis.
Rigano et al, Ionic Strength Dependence of Formation Constants. Anal. Chem, 1985, 57, 2956-2960.
Schwarzenbach, G., Complexometric Titations, Translated and revised by Harry Irving, p. 8, London, Chapman and Hall 1957.
Shen Zhen Guo et al., "Effects of Chelators EDTA and DTPA on the Uptake of Zinc, Copper, Manganese and Iron by Hyperaccumulator Thlaspi caerulescens", Acta Phytophysiologica Sinica, vol. 24, Issue 4, pp. 340-346, Dec. 31, 1998.
Shibata, Minako et al. Graduate School Environmental Earth Science, Hokkaido University, Sapporo, Japan, Acid-Catalyzed Copolymerization of Aspartic Acid with w-Amino Acid, Macromolecular Symposia (1998), 130, 229-244.

(Continued)

*Primary Examiner* — Bong-Sook Baek
(74) *Attorney, Agent, or Firm* — Karen A. Harding

(57) ABSTRACT

Ophthalmic compositions and methods of preparing such compositions are disclosed.

6 Claims, 2 Drawing Sheets

(56) References Cited

OTHER PUBLICATIONS

Smith, L.J.R, et al., Amine Oxidation. Part VII. The Effect of Structure on the Reactivity of Alkyl Tertiary Amines towards Alkaline Potassium Hexacyanoferrate-(III), J. Chem. Soc, Perkin Trans. II: Physical Organiz Chemistry. 1973, (2), 206.

Tang et al., 1996, The pH of mult-purpose soft contact lens solutions. Optom. Vis. Sci. 73:746-749.

Wang, Yun-Ming, et al. "Synthesis of some N, N"-bis(amide) derivatives of diethylenetriaminepentaacetic acid and the stabilities of their compleses with Gd, Ca, Cu and Zn" Journal of the Chemical Society, Dalton Trans, 1997 pp. 833-837.

Zhang Weilie et al., "Preparation of Ketotifen Fumarate Spraying Solution", Chinese Journal of Pharmaceuticals, vol. 32, Issue 5, pp. 205-207, Dec. 31, 2001.

PCT International Search Report, dated Feb. 25, 2008, for PCT Int'l Appln. No. PCT/US2007/064142.

Avunduk et al, Comparison of the Effects of Ketotifen Fumarate 0.025% and Olopatadine HCl 0.1% Ophthalmic Solutions in Seasonal Allergic Conjunctivitis: A 30-Day, Randomized, Double-Masked, Artificial Tear Substitute-Controlled Trial, Clinical Therapeutics, vol. 27, No. 9, pp. 1392-1402, 2005.

Lang, G. "Collagenase in Equine Cell Culture Preparation" Journal of Clinical Microbiology, Jun. 1979, vol. 9, No. 6, p. 731-733.

\* cited by examiner

METHODS FOR STABILIZING OXIDATIVELY UNSTABLE COMPOSITIONS

RELATED APPLICATION

This application is a division of currently pending U.S. patent application No. 11/868,988 filed Mar. 16, 2007 which is a non-provisional application of U.S. Patent Application No. 60/783,557 filed on Mar. 17, 2006, now expired. The complete disclosures of the aforementioned related U.S. patent applications are hereby incorporated herein by reference for all purposes.

This application claims priority from a non-provisional filing, U.S. App. Pat. No. U.S. App. Pat. No. 60/783,557 entitled "Methods for Stabilizing Oxidatively Unstable Pharmaceutical Compositions," which was filed on, Mar. 17, 2006.

FIELD OF THE INVENTION

This invention related to compositions of oxidatively unstable ophthalmic ingredients and methods for preparing such compositions

BACKGROUND

Therapeutic agents for topical administration to the eye are generally formulated in either a liquid or gel form and must be kept sterile until administration. Accordingly, ophthalmic therapeutic agents are either packaged aseptically, which is cumbersome and expensive or are heat sterilized. Unfortunately, many therapeutic agents are not oxidatively stable, especially at elevated temperatures.

EDTA, Dequest, and Desferal have been used to improve the stability of certain therapeutic agents during autoclaving. However, there remains a need for other compounds capable of stabilizing unstable therapeutic agents that are susceptible to oxidative degradation. This need is met by the following invention.

DETAILED DESCRIPTION OF THE INVENTION

Figure 1:
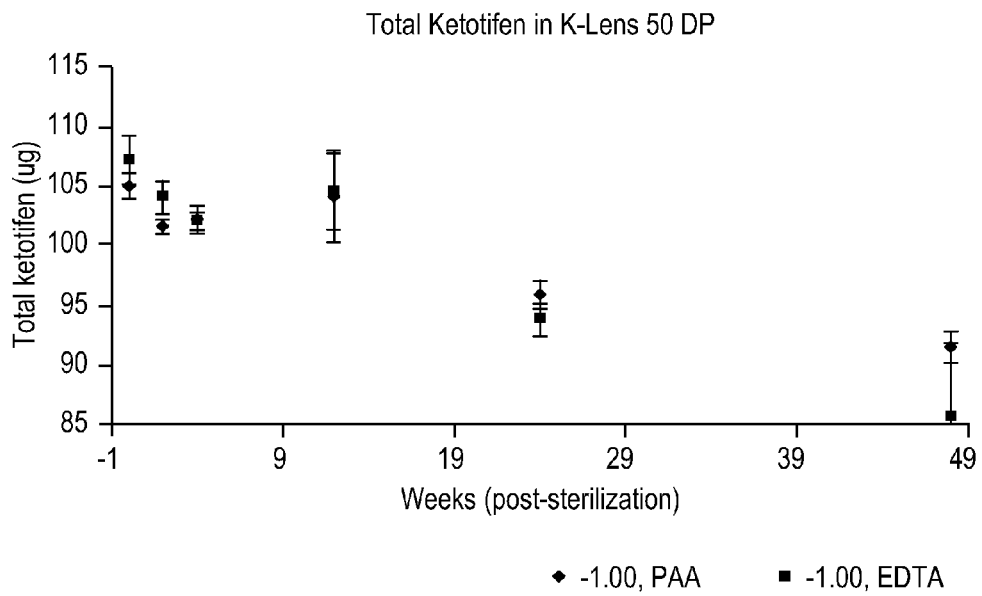
FIG. 1 Stability Study with Ketotifen and PAA or EDTA
FIG. 2. Stability Study with Ketotifen and PAA or EDTA
FIG. 3 Stability Study with Ketotifen and PAA or DTPA

This invention includes a method of stabilizing an ophthalmic composition comprising an oxidatively unstable pharmaceutical ingredient wherein said method comprises adding an effective amount of a stabilizing agent to the ophthalmic composition.

As used herein "oxidatively unstable pharmaceutical ingredient" refers to pharmaceutical or nutraceutical compounds used to treat conditions of the eye, and such compound degrade in the presence of oxygen and certain transition metals. Examples of pharmaceutical compounds include antihistamines, antibiotics, antibacterial agents, antiviral agents, antifungal agents, analgesics, anesthetics, antiallergeneic agents, mast cell stabilizers, steroidal and non-steroidal anti-inflammatory agents, angiogenesis inhibitors; antimetabolites, fibrinolytics, neuroprotective drugs, angiostatic steroids, mydriatics,cyclopegic mydriatics; miotics; vasoconstrictors; vasodilators, anticlotting agents; anticancer agents, antisense agents, immunomodulatory agents, carbonic anhydrase inhibitors, integrin antabonistsl; cyclooxygenase inhibitors, VEGF antagonists; immunosuppressant agents and the like. Particularly, examples of pharmaceutical agents include but are not limited to acrivastine, antazoline, astemizole, azatadine, azelastine, buclizine, bupivacaine, cetirizine, clemastine, cyclizine, cyproheptadine, ebastine, emedastine, ephedrine, eucatropine, fexofenadine, homatropine, hydroxyzine, ketotifen, levocabastine, levoceterizine, lomefloxacin, meclizine, mepivacaine, mequitazine, methdilazine, methapyrilene, mianserin, naphazoline norastemizole, norebastine, ofloxacin, oxymetazoline, pheniramine, phenylephrine, physostigmine, picumast, promethazine, scopolamine, terfenadine, tetrahydozoline, thiethylperazine, timolol, trimeprazine, triprolidine, pharmaceutically acceptable salts and mixtures thereof. Preferred pharmaceutical compounds include acrivatine, antazoline, astemizole, azatadine, azelastine, clemastine, cyproheptadine, ebastine, emedastine, eucatropine, fexofenadine, homatropine, hydroxyzine, ketotife, levocabastine, levoceterizine, meclizine, mequitazine, methdialazine, methapyrilene, norastemizole, norebastine, oxymetazoline, physootigmine, picumast, promethazine, scopolamine, terfenadine, tetrahyerozoline, fimilol, trimeprazine, triprolidine, and pharmaceutically acceptable salts thereof. Particularly preferred pharmaceutical compounds include phenarimine, ketotifen, ketotifen fumarate nor ketotifen, olapatadine and mixtures thereof. More particularly preferred pharmaceutical compounds include ketotifen, its pharmaceutically acceptable salts, and mixtures thereof.

Examples of nutraceutical compounds include vitamins and supplements such as vitamins A, D, E, lutein, zeaxanthin, lipoic acid, flavonoids, ophthalmicially compatible fatty acids, such as omega 3 and omega 6 fatty acids, combinations thereof, combinations with pharmaceutical compounds and the like. Preferred pharmaceutical or nutraceutical compounds are those that degrade when solutions of these compounds and oxidative catalysts (such as metals and metallic salts) are mixed together at ambient or elevated temperatures, as compared to solutions of these compounds without oxidative catalysts at ambient or elevated temperatures. Particularly preferred pharmaceutical or nutraceutical compounds are those that degrade greater than about 10% when heated to about 120° C. for about 20 minutes with oxidative catalysts. The concentration of oxidatively unstable pharmaceutical ingredients in the ophthalmic compositions of the invention range from about 2 µg/mL to about 0.5 g/mL, particularly preferred, about 0.1 µg/mL to about 10,000 µg/mL.

The term "ophthalmic composition" refers to liquids, aerosols, or gels that may be topically administered to the eye. The term "stabilizing agent" refers to chelant compositions that inhibit metal catalyzed oxidative degradation of the oxidatively unstable pharmaceutical ingredient. Examples of stabilizing agents include but are not limited to silica, chitin derivative such as chitosan, polyamides such as poly(aspartic acid-co-ω-amino acid) (See CAN:129:54671, Shibata, Minako et al. Graduate School Environmental Earth Science, Hokkaido University, Sapporo, Japan Macromolecular Symposia (1998), 130, 229-244) and polymeric amides such as poly[iminocarbonyl(2,5-dihydroxy-1,4-phenylene)carbonylimino-1,4-phenylenemethylene-1,4-phenylene], CAS #87912-00-3, polymeric lactams such as polyvinylpyrrolidone, polyamino carboxylic acids such as diethylenetriaminepentaacetic acid and triethylenetriaminepentaacetic acid, polymeric amines such as polyallylamine, crown ethers such as 18-crown-6, 21-crown-7, and 24-crown-8, cellulose and its derivatives, and N,N,N',N',N'', N"-hexa(2-pyridyl)-1,3,5-tris(aminomethyl)benzene, and certain macrocyclic ligands such as crown ethers, ligand containing knots and catenands (See, David A. Leigh et al *Angew. Chem Int. Ed.*, 2001, 40, No. 8, pgs. 1538-1542 and Jean-Claude Chambron et al. *Pure & Appl. Chem.*, 1990, Vol. 62, No. 6, pgs. 1027-1034) The preferred stabilizing agents are polyamino carboxylic acids such as diethylenetriaminepentaacetic acid and triethylenetriaminepentaacetic acid. The particulary preferred stabilizing agents are diethylenetriaminepentaacetic acid ("DTPA"), or salts of DTPA such as $CaNa_3DTPA$, $ZnNa_3DTPA$, and $Ca_2DTPA$. The term "effective amount" refers to the amount of stabilizing agent required to inhibit the oxidative degradation of the pharmaceutical ingredient. In most circumstances it is preferred that there is a 1:1 molar ration of metal present in the ophthalmic composition to chelant, is more preferably about 1 of metal to greater than about 1 of chelant compositions, most preferably about 1 of metal to greater than or equal to about 2 of chelant compositions. With respect to concentration limits, it is preferred that the stabilizing agents have a concentration in the ophthalmic composition from about 2.5 μmoles/liter to about, 5000 μmoles/liter more preferably from about 20 μmoles/liter to about 1000 μmoles/liter, more preferably from about 100 μmoles/liter to about 1000 μmoles/liter, most preferably from about 100 μmoles/liter to about 500 μmoles/liter.

Aside from the oxidatively unstable pharmaceutical ingredient and the stabilizing agent, the ophthalmic composition contains suitable ophthalmic carriers. Suitable carriers include antioxidants (radical scavengers), demulcents, antibacterial agents, solubilizers, surfactants, buffer agents, tonicity adjusting agents, chelating agents, preservatives, wetting agents, thickeners, water, saline solution, mineral oil, petroleum jelly, water soluble solvents, such as $C_{15-20}$ alcohols, $C_{15-20}$ amides, $C_{15-20}$ alcohols substituted with zwitterions, vegetable oils or mineral oils comprising from 0.5 to 5% by weight hydroxyethylcellulose, ethyl oleate, carboxymethylcellulose, polyvinylpyrrolidone and other non-toxic water-soluble polymers for ophthalmic uses, such as, for example cellulose derivatives, such as methylcellulose, alkali metal salts of carboxy-methylcellulose, hydroxymethylcellulose, hydroxyethylcellulose, methylhydroxypropyl-cellulose, hydroxypropylcellulose, chitosan and scleroglucan, acrylates or methacrylates, such as salts of poly(acrylic acid) or ethyl acrylate, polyacrylamides, natural products, such as gelatin, alginates, pectins, tragacanth, karaya gum, xanthan gum, carrageenin, agar and acacia, starch derivatives, such as starch acetate and hydroxypropyl starch, and also other synthetic products, such as poloxamers, e.g. Poloxamer F127, polyvinyl alcohol, polyvinylpyrrolidone, polyvinyl methyl ether, polyethylene oxide, preferably cross-linked poly(acrylic acid), such as neutral Carbopol, or mixtures of those polymers. Preferred carriers are water, cellulose derivatives, such as methylcellulose, alkali metal salts of carboxymethylcellulose, hydroxymethylcellulose, hydroxyethylcellulose, methylhydroxypropylcellulose and hydroxypropylcellulose, neutral Carbopol, or mixtures thereof. The concentration of the carrier is, for example, from 0.1 to 100000 times the concentration of the active ingredient combinations thereof and the like. When the ophthalmic composition is an eye drop, preferred carriers include water, pH buffered saline solution, mixtures thereof and the like. The preferred carrier is an aqueous saline solution containing salts including, without limitation, sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. The buffered solutions may additionally include 2-(N-morpholino)ethanesulfonic acid (MES), sodium hydroxide, 2,2-bis(hydroxymethyl)-2,2',2"-nitrilotriethanol, n-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid and the like and combinations thereof. Most preferably, the carrier is a borate buffered or phosphate buffered saline solution.

Further the invention includes an ophthalmic composition comprising an oxidatively unstable pharmaceutical ingredient and an effective amount of a stabilizing agent. The terms oxidatively unstable pharmaceutical ingredient, effective amount, and stabilizing agents all have their aforementioned meanings and preferred ranges.

Still further the invention includes a method of stabilizing an ophthalmic composition comprising an oxidatively unstable excipient wherein said method comprises adding an effective amount of a stabilizing agent to the ophthalmic composition.

As used herein "oxidatively unstable excipient" refers to a component of ophthalmic compositions that degrades in the presence of oxygen and certain transition metals. Examples of unstable excipients include but are not limited to astringents, demulcents, emollients, hypertonicity agents, oleaginous, agents, tonicity agents mucomimetic agents, and the like. Particularly examples of unstable excipients include but are not limited to cellulose derivatives, carboxymethylcellulose, hydroxyethylcellulose, hydroxypropylcellulose, hyaluronic acid, methylcellulose, Dextran, gelatin, polyols, glycerin, polyethylene glycol, polysorbate, propylene glyxol, polyvinyl alcohol, povidone lanolin, mineral oil, paraffin, petrolatum, white ointment, white petrolatum, white, wax, and yellow wax. The terms "stabilizing agent," and "effective amount" have their aforementioned meanings and preferred ranges.

Yet still further the invention includes an ophthalmic composition comprising an oxidatively unstable excipient and an effective amount of a stabilizing agent. The terms "oxidatively unstable excipient," "stabilizing agent," and "effective amount" have their aforementioned meanings and preferred ranges.

Even further still the invention includes a method of stabilizing an ophthalmic composition comprising an oxidatively unstable pharmaceutical ingredient wherein said method comprises
 (a) functionalizing said stabilizing agent with a polymerizable group,
 (b) polymerizing an effective amount of the product of step (a) with at least one type of polymerizable monomer, and
 (c) contacting the ophthalmic composition comprising an oxidatively unstable pharmaceutical ingredient with the polymer of step (b).

The terms oxidatively unstable pharmaceutical ingredient, effective amount, and stabilizing agents all have their aforementioned meanings and preferred ranges. The term functionalizing means chemically bonding a polymerizable group to said stabilizing agent. Examples of a polymerizable group includes but are not limited to methacrylate, acrylate, acrylamide, and styrene. The term polymerizable monomer includes compounds containing olefinic moieties capable of adding to radical species, such as propylene, ethylene and the like. The polymerization product of step (b) may be soluble or insoluble in the ophthalmic composition. It is preferred that the polymerization product of step (b) is not soluble in the ophthalmic composition and as such the polymerization product of step (b) may be in any form such as rods, discs, containers, films and the like.

Even further still the invention includes a method of stabilizing an ophthalmic composition comprising an oxidatively unstable excipient wherein said method comprises
  (a) functionalizing said stabilizing agent with a polymerizable group,
  (b) polymerizing an effective amount of the product of step (a) with at least one type of polymerizable monomer, and
  (c) contacting the ophthalmic composition comprising an oxidatively unstable exicipient with the polymer of step (b).

The terms oxidatively unstable excipient, effective amount, stabilizing agents, polymerizable group, and polymerizable monomers all have their aforementioned meanings and preferred ranges.

Further still the invention includes a container for an ophthalmic composition comprising an oxidatively unstable pharmaceutical ingredient wherein said container comprises the polymerization product of an effective amount of a stabilizing agent functionalized with a polymerizable group and at least one type of polymerizable momoner. The terms oxidatively unstable pharmaceutical ingredient, effective amount, stabilizing agents, polymerizable group, and polymerizable monomers all have their aforementioned meanings and preferred ranges.

Yet, further still the invention includes a container for an ophthalmic composition comprising an oxidatively unstable excipient wherein said container comprises the polymerization product of an effective amount of a stabilizing agent functionalized with a polymerizable group and at least one type of polymerizable momoner. The terms oxidatively unstable excipient, effective amount, stabilizing agents, polymerizable group, and polymerizable monomers all have their aforementioned meanings and preferred ranges.

The advantages of the compositions and methods of this invention are numerous. First ketotifen is known as a oxidatively unstable pharmaceutical ingredient. Compositions containing ketotifen fumarate are known. These compositions contain EDTA and the pH of those compositions is about 5.5. These EDTA solutions stabilize the ketotifen fumarate against oxidative degradation, the pH of these solutions is below the threshold for ocular awareness and it is likely that some patient who use this solution will be uncomfortable due to low pH value of the solution. See Tang, I., Wong, D. M., Yee, D. J. and Harris, M. G. 1996 The pH of multi-purpose soft contact lens solutions. Optom. Vis. Sci. 73:746-749. Adler, F. H. 1959 Physiology of the Eye. Third edition. p. 40. Brawner, L. W. and Jessop, D. G. 1962. A review of contact lens solutions. Contacto 6:49-51. It has been discovered that the stabilizing agents of the invention will reduce the degradation of ketotifen fumarate at higher pH values that those of ketotifen fumarate solutions containing EDTA. The pH of ophthalmic compositions of the invention is preferably between about pH 6.6 and about pH 7.2, more preferably between about pH 6.8 and about pH 7.0.

Second it has been shown that the shelf life of ketotifen fumarate solutions containing DTPA are superior to the shelf life of ketotifen fumarate solutions containing either EDTA or PAA. Third, it is known that the application of heat increases the rate of degradation of many pharmaceutical ingredients. It has been shown that the stabilizing agents of this invention are useful in reducing degradation associated with higher temperature, such as sterilization temperatures.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

EXAMPLES

The following abbreviations are used below
PAA
  Polyacrylic Acid, sodium salt having an average molecular weight of 200,000
EDTA
  Ethylenediamine tetraacetic acid.
Solution A
  Deionized water containing the following ingredients by weight: NaCl (0.83%), Boric Acid (0.91%), Sodium tetraborate decahydrate (0.1%)
Initial Testing to Determine Suitability of Ingredients It is known that excessive quantities of certain transition metals and their salts will degrade ketotifen fumarate. The amount of metals and salts contained within commercially available ingredients varies, so test batches of Solution A were evaluated as follows. 200 g Solution A was mixed at ambient temperature and ketotifen fumarate (5 mg±2 mg) was added and mixed until homogenous. Six glass vials were filled with 3 mL of this solution. The vials were stopped with poly tetrafluoroethylene ("PTFE") and three of the vials were heated for eighteen minutes at 124° C. Samples of each treated vial (1.0-1.5 mL) were analyzed by HPLC and compared to the untreated controls. If the amount of ketotifen in the treated vials reduced by less than or equal to five percent (≤5%) the ingredients were determined to be suitable for further studies and larger batches of Solution A were prepared from these ingredients.

Example 1

Preparation of Ketotifen Fumarate Solutions with PAA, EDTA

Figure 2:
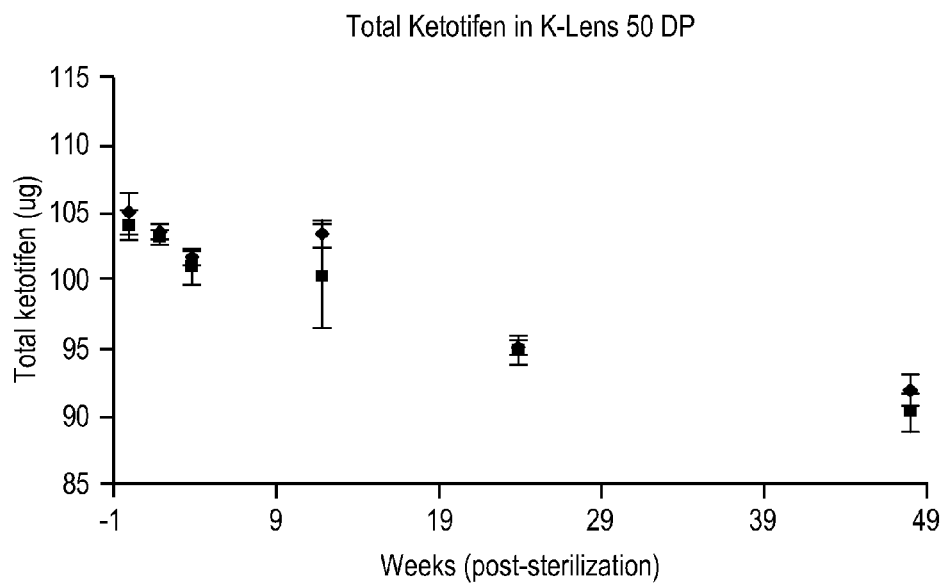

PAA (2000 µg/mL) was added to Solution A, and 50 µg/mL of ketotifen fumarate (approximately 36 µg/mL of ketotifen) was dissolved in the system. EDTA (100 µg/mL) was added to another batch of Solution A, and 50 µg/mL of ketotifen fumarate was dissolved in the system. Negative One and negative twelve (−1.0 and 12.0) diopter etafilcon A contact lenses were added to vials containing 3 mL of each of the above solutions. The vials were sealed with PTFE coated rubber stoppers, sterilized at 124° C. for 18 minutes, and stored at ambient temperature for one year. Samples were harvested throughout the year and analyzed for the presence of ketotifen by HPLC. The results are presented in FIGS. 1 and 2. These results show that there is substantial degradation of the ketotifen over time with PAA and with EDTA.

Example 2

Preparation of Ketotifen Fumarate Solutions with PAA, DTPA

Figure 3:
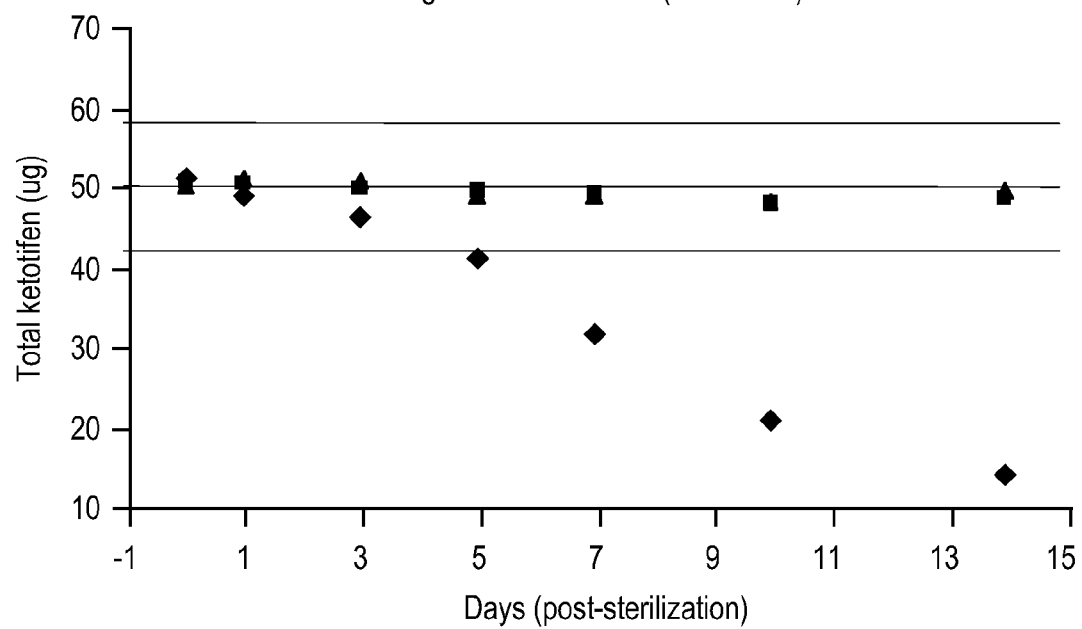

To separate batches of Solution A, Ca$_2$DTPA (100 µg/mL and 300 µg/mL, 213 and 640 µmoles/L respectively) and 2000 μg/mL (0.2%, approximately 18.51 mmole/L methacrylate content) of PAA were added, and approximately 25 μg/mL of ketotifen fumarate (approximately 18 μg/mL of ketotifen) was dissolved in each of the systems. Three mL samples of each solution were added to individual vials containing contact lenses. Each set of vials was closed with PTFE stoppers, sterilized at 124° C. for 18 minutes, and stored at 80° C. for a period of two weeks. Samples were harvested at various intervals and analyzed for the presence of ketotifen by HPLC. The results are presented in FIG. 3. These results show that there is substantial degradation of the ketotifen over time with PAA but not with the calcium salt of DTPA Example 3

Ketotifen Fumarate Solutions with Oxidation Catalysts

Ketotifen fumarate (50 μg/mL, approximately 36 μg/mL of ketotifen) was dissolved in Solution A containing approximately 500 μg/mL of either DTPA (approximately 1272 μmoles/L of DTPA) or the sodium salt of EDTA ($Na_2C_{10}H_{14}O_8N_2 \cdot 2H_2O$, 1344 μmoles/L of EDTA). Approximately 50 μg/mL of the salts listed in Table 1 were dissolved in each of the solutions and about 3 mL of each solution was dosed into several vials The vials were sealed with PTFE coated rubber stoppers and were subjected to zero, one, two or three sterilization cycles as indicated in Table 1. One sterilization cycle is eighteen minutes of heating at 124° C. Samples were analyzed by HPLC for the concentration of ketotifen at the intervals indicated in Table 2. This data shows that in the presence of oxidative catalysts, DTPA reduces the amount of oxidative degradation as compared to EDTA.

TABLE 1

| [salt] (ug/mL) | Metal salt | Solution |
| --- | --- | --- |
| 16 | $MnSO_4 \cdot H_2O$ | Manganese |
| 18 | $KMnO_4$ | solutions |
| 16 | $MnOAc_3$ | |
| 25 | $FeSO_4 \cdot 7H_2O$ | Iron solutions |
| 25 | $Fe_2O_{12}S_3 \cdot nH_2O$ | |

TABLE 1-continued

| [salt] (ug/mL) | Metal salt | Solution |
| --- | --- | --- |
| 25 | $NiSO_4 \cdot 7H_2O$ | Nickel solutions |
| 25 | $NiF_6K_2$ | |
| 25 | $CuSO_4$ | Copper |
| 26 | $Cu_2O$ | solutions |

TABLE 2

| # cycles | DTPA stabilized systems | | | | EDTA stabilized systems | | | |
| --- | --- | --- | --- | --- | --- | --- | --- | --- |
| | Fe | Cu | Ni | Mn | Fe | Cu | Ni | Mn |
| 0 | 36.29 | 36.35 | 36.40 | 35.57 | 36.15 | 35.78 | 36.34 | 33.54 |
| 1 | 35.14 | 36.13 | 36.48 | 34.33 | 19.41 | 35.33 | 34.46 | 23.98 |
| 2 | 34.10 | 36.19 | 36.10 | 33.71 | 12.84 | 34.89 | 32.75 | 18.01 |
| 3 | 33.28 | 35.92 | 36.22 | 33.34 | 7.73 | 34.71 | 29.91 | 12.89 |

What is claimed is:

1. An ophthalmic composition comprising a liquid, aerosol or gel which comprises, and an oxidatively unstable pharmaceutical ingredient selected from the group consisting of ketotifen, its pharmaceutically acceptable salts, nor ketotifen fumarate, and mixtures thereof and an effective amount of a stabilizing agent selected from the group consisting of diethylenetriaminepentaacetic acid and salts of diethylenetriaminepentaacetic acid wherein the ophthalmic composition has a pH of 6.6 to 7.2.

2. The ophthalmic composition of claim 1 wherein the effective amount of the stabilizing agent is about 2.5 μmoles/liter to about 5000 μmoles/liter.

3. The ophthalmic composition of claim 1 wherein the effective amount of the stabilizing agent is about 100 μmoles/liter to about 1000 μmoles/liter.

4. The ophthalmic composition of claim 1 wherein the effective amount of the stabilizing agent is about 100 μmoles/liter to about 600 μmoles/liter.

5. The ophthalmic composition of claim 1 wherein the stabilizing agent is diethylenetriaminepentaacetic acid.

6. The ophthalmic composition of claim 1 wherein the oxidatively unstable pharmaceutical ingredient is selected from the group consisting of ketotifen, its pharmaceutically acceptable salts, and mixtures thereof.

* * * * *